United States Patent [19]

Matsunaga et al.

[11] Patent Number: 5,693,610
[45] Date of Patent: Dec. 2, 1997

[54] BINDING AGENT FOR GROWTH FACTOR

[75] Inventors: Kenichi Matsunaga, Saitama; Yoshiharu Oguchi; Minoru Ohara, both of Tokyo, all of Japan

[73] Assignee: Kureha Chemical Industry Co., Ltd., Tokyo, Japan

[21] Appl. No.: 519,023

[22] Filed: Aug. 24, 1995

[30] Foreign Application Priority Data

Aug. 25, 1994 [JP] Japan .................. 6-224281

[51] Int. Cl.⁶ .......................... A61K 38/02; C07K 14/375
[52] U.S. Cl. .......................... 514/8; 530/395
[58] Field of Search .................. 530/595; 514/8

[56] References Cited

U.S. PATENT DOCUMENTS 4,975,422  12/1990  Kanoh et al. .............. 514/54

FOREIGN PATENT DOCUMENTS

| | | |
|---|---|---|
| 60-045524 | 3/1985 | Japan . |
| 60-045525 | 3/1985 | Japan . |
| 60-045526 | 3/1985 | Japan . |
| 60-045528 | 3/1985 | Japan . |
| 60-045529 | 3/1985 | Japan . |
| 60-45523 | 3/1985 | Japan . |
| 60-45527 | 3/1985 | Japan . |
| 60-45530 | 3/1985 | Japan . |
| 60-45531 | 3/1985 | Japan . |
| 60-45532 | 3/1985 | Japan . |
| 60-45533 | 3/1985 | Japan . |
| 60-139622 | 7/1985 | Japan . |
| 2-011521 | 1/1990 | Japan . |
| 3-109331 | 5/1991 | Japan . |
| 6-157333 | 6/1994 | Japan . |

*Primary Examiner*—Jeffrey E. Russel
*Attorney, Agent, or Firm*—Sughrue, Mion, Zinn, Macpeak & Seas, PLLC

[57] ABSTRACT

A binding agent for a growth factor selected from the group consisting of transforming growth factor-β (TGF-β) and platelet-derived growth factor (PDGF), comprising a protein-bound polysaccharide which is obtained from a fungus belonging to Coriolus, and contains about 18 to 38% by weight of proteins, and a pharmaceutically acceptable carrier or diluent is disclosed.

3 Claims, 6 Drawing Sheets

BINDING AGENT FOR GROWTH FACTOR

BACKGROUND OF THE INVENTION

1. Field of the Invention

The present invention relates to a binding agent for particular growth factors, namely, transforming growth factor-β (TGF-β) and platelet-derived growth factor (PDGF). The binding agent of the present invention selectively binds to the particular growth factors to inhibit their biological activities. Therefore, the binding agent of the present invention can be used for treatment or prevention of various diseases directly or indirectly caused by the particular growth factors.

2. Description of the Related Art

Various factors which are produced in a living body and act on a particular cell to promote its growth have been found, and the structures and the functions thereof have been elucidated. It has been discovered that some growth factors exhibit not only the promotion of the growth, but also the various biological activities, and that the overproduction and/or abnormal metabolism of such factors are involved in various diseases.

Transforming growth factor-β (TGF-β) and platelet-derived growth factor (PDGF) belong to such a growth factor. TGF-β was first found as a factor to promote growth of a rat fibroblast. Thereafter, it has been found that TGF-β inhibits growth of a lot of cells, strongly suppresses immunological activity, and increases extracellular matrix. It is suggested that the overproduction and/or abnormal metabolism of TGF-β are involved in various diseases and symptoms of immunosuppression in a cancer patient or the like, fibroid lung, hepatic fibrosis, glomerulonephritis, scleroderma, or the like. Further, PDGF acts on smooth muscle cells, fibroblasts, nerve gliacytes or the like to promote their growth. The relationship between PDGF and arterial sclerosis caused by wandering and growth of vascular smooth muscle cells attracts attention.

It would be possible to use an antibody which specifically binds to TGF-β and/or PDGF to inhibit their functions, as a means of inhibiting the functions of the growth factors. In fact, the attempts to use such an antibody were actually made. Nevertheless, when the antibody is administered, there exist many problems to be solved, for example, prevention of allergic reaction caused by the administration, or prevention of the activity reduction by the production of antibodies to neutralize the administered antibody. Therefore, it is desired to develop an agent which inhibits the function of the growth factors, and can be safely administered.

SUMMARY OF THE INVENTION

The inventors of the present invention engaged in intensive studies to solve the above problems, and as a result, found that the particular protein-binding polysaccharide which is obtained from Basidiomycetes, and which has been clinically used as a carcinostatic agent and proved to hardly produce side-effects, binds to the above growth factors to inhibit the functions thereof. The present invention is based on the findings.

Accordingly, the object of the present invention is to provide a binding agent for the above growth factors.

Other objects and advantages will be apparent from the following description.

In accordance with the present invention, there is provided a binding agent for a growth factor selected from the group consisting of transforming growth factor-β (TGF-β) and platelet-derived growth factor (PDGF), comprising a protein-bound polysaccharide which is obtained from a fungus belonging to Coriolus, and contains about 18 to 38% by weight of proteins.

DESCRIPTION OF THE PREFERRED EMBODIMENTS

The protein-bound polysaccharide used as an active ingredient in the binding agent of the present invention is disclosed in, for example, Japanese Examined Patent Publications (Kokai) No. 46-17149, No. 51-36322, No. 56-14274, No. 56-14275, and No. 56-14276. The protein-bound polysaccharide is an extract from mycelia, broth, or fruit bodies that is obtained by culturing the fungus belonging to Coriolus, which belongs to Basidiomycetes. The protein-bound polysaccharide contains about 18 to 38% by weight of proteins, and has a molecular weight of not less than 5,000, preferably 5000 to 3000,000. Further, the protein-bound polysaccharide is described in "Saikin no Shinyaku (Recent New Medicines)", Vol. 28, 14–16, 1977; and Vol. 29, 96–101, 1978; and "Iyakuhin Yoran (Handbook of Medicines)", 6th Ed., 1346, 1979, published by Yakuji Jiho Publishing Co.

A typical example of the protein-bound polysaccharide is called PSK, which is commercially available as "KRES-TIN" (trade mark) from Sankyo Co., Ltd.

The properties of PSK are as follows:

PSK may be prepared by extracting the mycelia of Coriolus versicolor (Fr.) Quél [FERM-P2412 (ATCC20547)] with hot water, purifying and then drying the extract. The average molecular weight (ultracentrifugal method) is about 100,000. The sugar portion in the major fractions is $\beta$-D-glucan. The glucan has a branched structure containing 1→3, 1→4 and 1→6 bonds, and mainly comprises glucose (74.6% by weight) and mannose (15.5% by weight). In the amino acid composition of the proteins, there are many acidic amino acids, such as aspartic and glutamic acids, many neutral amino acids, such as valine and leucine, but a few basic amino acids, such as lysine and arginine. PSK is soluble in water, but hardly soluble in methanol, pyridine, chloroform, benzene or hexane. PSK begins to be gradually decomposed at about 120° C.

The protein-bound polysaccharide is extremely safe, because of very low toxicity and few side-effects. The acute toxicity of PSK is shown in the following Table 1.

TABLE 1

| Animal sp. | Route | $LD_{50}$ (mg/kg) Male | $LD_{50}$ (mg/kg) Female |
|---|---|---|---|
| Mice | per os | >20000 | >20000 |
| Rats | per os | >20000 | >20000 |

The acute toxicity shown in Table 1 was determined by the following method. The 4- or 5-week-old ICR-JCL mice (21 to 24 g) and the 4- or 5-week-old Donryu rats (100 to 150 g) were used. The agent was orally administered as shown in Table 1. The protein-bound polysaccharide was dissolved in physiological saline and the solution was administered. Death and body weight were observed for 7 days. Thereafter, the animals were sacrificed for autopsy. No death was observed in mice and rats even by the maximum administrable doses, and thus, the determination of $LD_{50}$ was substantially impossible.

The protein-bound polysaccharide used as an active ingredient in the binding agent of the present invention selectively binds to TGF-$\beta$ and PDGF, but does not bind to various cytokines including growth factors other than TGF-$\beta$ and PDGF. For example, as shown in Examples 1 and 2, the protein-bound polysaccharide does not bind to epidermal growth factor (EGF); interleukin (IL)-1$\alpha$, IL-1$\beta$, IL-2, IL-3, IL-4, IL-6, IL-7, IL-8, or IL-10; tumor necrosis factor (TNF)-$\alpha$ or TNF-$\beta$; interferon (IFN)-$\alpha$, IFN-$\beta$, or IFN-$\gamma$; granulocyte colony-stimulating factor (G-CSF); or granulocyte-macrophage colony-stimulating factor (GM-CSF).

The TGF-$\beta$ which binds to the protein-bound polysaccharide is not limited, but includes, for example, TGF-$\beta_1$, TGF-$\beta_2$, TGF-$\beta_3$, TGF-$\beta_4$, and TGF-$\beta_5$.

The protein-bound polysaccharide used as an active ingredient in the binding agent of the present invention inhibits the physiological activity of TGF-$\beta$ and PDGF by selectively binding thereto. This will be concretely demonstrated in Examples 3 and 4 (in vitro) and Example 5 (in vivo), respectively. More particularly, when TGF-$\beta$ is added to an in vitro growth reaction culture of cells highly sensitive to TGF-$\beta$ (i.e., the fetal mink lung cell line Mv1Lu and the mouse T cell line CTLL-2), the growth of the cells is inhibited. If the protein-bound polysaccharide is added in advance to the in vitro growth reaction culture, the inhibitory action of TGF-$\beta$ is reduced. The binding of TGF-$\beta$ to the cells is also inhibited. Further, in the in vivo experiment of mice to which leukemic cells are implanted, the tumor growth promoted by administering TGF-$\beta$ is inhibited by administering PSK.

As above, the protein-bound polysaccharide selectively binds only to the particular growth factors, i.e., TGF-$\beta$ and PDGF, and thus, the function of the protein-bound polysaccharide is limited to the inhibition of the physiological activities of bound TGF-$\beta$ and PDGF only. Therefore, it is believed that no side-effect caused by any inhibition of functions of other growth factors is produced. Further, the protein-bound polysaccharide has extremely low toxicity, and has been clinically proved to hardly produce side-effect. Thus, it may be safely administered for a long period of time.

When the binding agent of the present invention is administered to an animal including human as an inhibitor of TGF-$\beta$ and/or PDGF, the binding agent may be formulated into a composition for various routes, such as a composition for oral administration, injections for subcutaneous, intravenous, or intramuscular administration, or a suppository for rectal administration. The composition for oral administration is, for example, tablet, granule, powder, or capsule. The composition may contain a binder, excipient, lubricant, disintegrating agent, or wetting agent. The oral liquid composition may be in the form of mixture for internal use, shaking mixture, suspension, emulsion, or syrup, or in the form of a dry product which should be re-dissolved when used. Further, the above oral liquid composition may contain an additive or preservating agent. A parenteral composition, such as injection, suppository, or ointment, may contain an additive, such as a stabilizing agent, buffer, preservating agent, or isotonicity. The composition may be in the form of an aqueous solution, suspension, solution, or emulsion in oily or aqueous vehicle. Alternatively, the active ingredient may be in the form of powder which should be re-dissolved in a suitable vehicle, such as sterilized water without a pyrogenic substance, when used.

The dose of the binding agent may vary with administration routes, ages, individual differences, or symptoms, but in general, 0.5 to 1000 mg/kg weight/day. In an oral administration, a dose of 20 to 1000 mg may be administered once or divided into two or three.

EXAMPLES

The present invention will now be further illustrated by, but is no means limited to, the following Examples.

Example 1

To a vial containing 1 µg of lyophilized human TGF-$\beta_1$ (Takara Shuzo), 5 mM HCl (100 µl) containing bovine serum albumin (2 mg/ml) was added to dissolve human TGF-$\beta_1$. Then, 9.9 ml of phosphate buffered physiological saline (pH 7.4) containing bovine serum albumin (2 mg/ml) was added thereto to prepare a TGF-$\beta_1$ solution (100 ng/ml).

Further, PSK (Trademark "Krestin"; Sankyo) was dissolved in phosphate buffered physiological saline (pH 7.4) containing bovine serum albumin (2 mg/ml) to prepare PSK solutions containing 0.1 µg/ml, 0.5 µg/ml, 1.0 µg/ml, 5.0 µg/ml, 10 µg/ml, 50 µg/ml, 100 µg/ml, 500 µg/ml or 1000 µg/ml of PSK.

The above TGF-$\beta_1$ (100 ng/ml) solution (100 µl) and the PSK (0.1 to 1000 µg/ml) solution (100 µl) were mixed in a test tube, and reaction was performed at 22° C. for 3 hours.

After the reaction was completed, the TGF-$\beta_1$ content in the mixed solution was measured by a commercially available Enzyme Immunoassay kit (TGF-$\beta_1$ ELISA System; Amersham Japan). The results are shown by closed circle (●) in FIG. 1. Further, the results by radioimmunoassay using $^{125}$I labeled anti-TGF-$\beta_1$ antibodies are shown by open circle (○) in FIG. 1. The binding ratio (%) in the axis of FIG. 1 is calculated from the equation (I):

$$\text{Binding ratio (\%)} = (Cc - Cp)/Cc \times 100 \tag{I}$$

wherein Cc is a measured content of TGF-$\beta_1$ in control groups, and Cp is a measured content of TGF-$\beta_1$ in PSK-addition groups.

Figure 1:
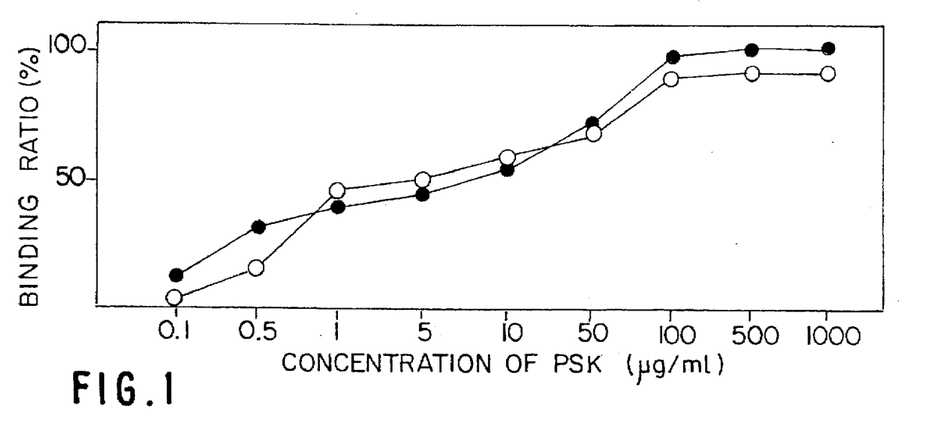
FIG. 1 is a graph showing the results of an enzyme-immunoassay (●) and radio-immunoassay (○) of the binding of TGF-β and PSK by the reaction therebetween, as carried out in Example 1.

As apparent from FIG. 1, the TGF-$\beta_1$ content in PSK-addition groups is dose-dependently lowered in comparison with that in control groups. Thus, it is manifest that PSK binds to the epitope of TGF-$\beta_1$.

The binding activities of PSK and various cytokines and growth factors other than TGF-$\beta$ were measured, using commercially available assay kit. The results in Table 2 clearly show that PDGF binds to PSK, as is the case with TGF-$\beta$, but PSK does not bind to other cytokines or growth factors. The binding ratio (%) in Table 2 were calculated from the equation (I).

TABLE 2

| Growth factor/Cytokine | | Binding ratio (%) PSK concentration (µg/ml) | | |
|---|---|---|---|---|
| (available from) | | 1 | 10 | 100 |
| rhTGF-$\beta_1$ | (1) | 32 | 68 | 96 |
| nhTGF-$\beta_1$ | (1) | 20 | 67 | 83 |
| rhTGF-$\beta_1$ | (2) | 0 | 0 | 0 |
| rhEGF | (3) | 0 | 0 | 0 |
| rhPDGF | (3) | 11 | 26 | 54 |
| rhIL-1α | (2) | 0 | 0 | 0 |
| rhIL-1β | (3) | 0 | 0 | 0 |
| rhIL-2 | (3) | 0 | 0 | 0 |
| rhIL-3 | (3) | 0 | 0 | 0 |
| rhIL-4 | (2) | 0 | 0 | 0 |
| rhIL-6 | (2) | 0 | 0 | 0 |
| rhIL-7 | (2) | 0 | 0 | 0 |
| rhIL-8 | (2) | 0 | 0 | 0 |
| rmIL-10 | (2) | 0 | 0 | 0 |
| rhTNF-α | (2) | 0 | 0 | 0 |
| rhTNF-β | (3) | 0 | 0 | 0 |
| rhIFN-β | (2) | 0 | 0 | 0 |
| rhIFN-γ | (4) | 0 | 0 | 0 |
| rhG-CSF | (2) | 0 | 0 | 0 |
| rhGM-CSF | (5) | 0 | 0 | 0 | n = natural; r = recombinant; h = human; m = mouse
Makers of enzyme immunoassay kit
(1) = Amersham Japan
(2) = R & D (USA)
(3) = kit from Otsuka Seiyaku
(4) = kit from Toray-Fuji
(5) = Oncogene Science

Example 2

To a vial containing 370 kBq (10 µCi) of $^{125}$I labeled human recombinant TGF-$\beta_1$ (74–167 TBq/mmol; Daiichi Kagaku Yakuhin), 1.0 ml of phosphate buffered physiological saline (pH 7.4) containing bovine serum albumin (2 mg/ml) was added to prepare a solution of $^{125}$I labeled TGF-$\beta_1$.

Then, PSK (Sankyo) was dissolved in phosphate buffered physiological saline (pH 7.4) containing bovine serum albumin (2 mg/ml) to prepare a solution of PSK (200 µg/ml).

In a test tube, 500 µl of the $^{125}$I labeled TGF-$\beta_1$ solution and 500 µl of the solution of PSK (200 µg/ml) or phosphate buffered physiological saline (pH 7.4) containing bovine serum albumin (2 mg/ml). Then, the reaction was performed at 22° C. for 3 hours.

After the reaction was completed, the reaction mixture was applied on a gel filtration column (diameter=1 cm; height=50 cm) filled with Bio-GelP-60 (Nihon Bio-Rad Laboratories) to carry out gel filtration chromatography. As an eluting solution, phosphate buffered physiological saline (pH 7.4) containing 0.1% bovine serum albumin was used. Each of the eluates was collected in 1 ml portions by a fraction collector, and the radioactivities were measured by a gamma counter.

Figure 2:
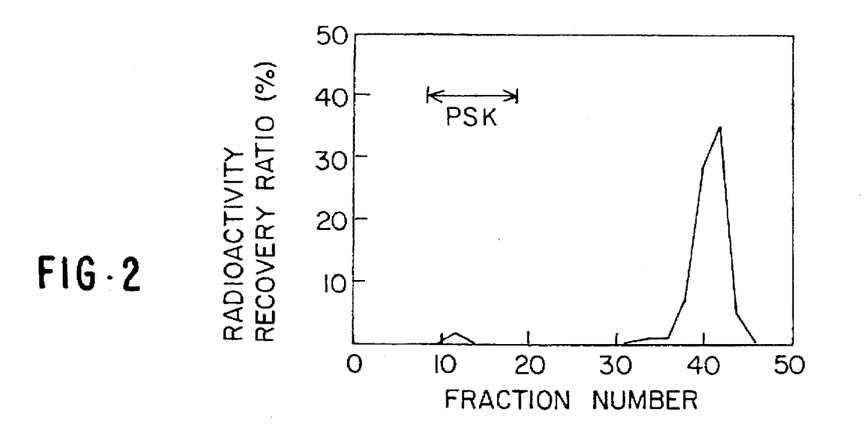
FIG. 2 is a graph showing the results of the control experiments using only $^{125}$I labeled TGF-$β_1$, in the experiments wherein $^{125}$I labeled TGF-$β_1$ was reacted with PSK, the reaction mixture was applied on a gel filtration chromatography column, and the radioactivities in fractions were measured as carried out in Example 2.
Figure 3:
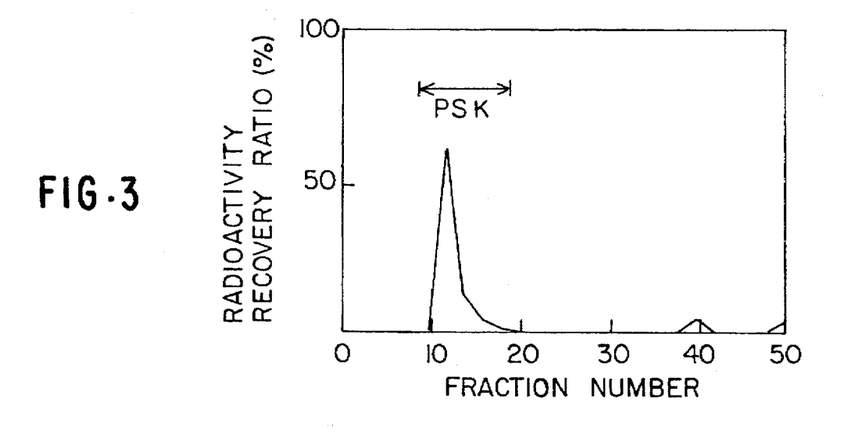
FIG. 3 is a graph showing the results of the case that $^{125}$I labeled TGF-$β_1$ and PSK were added, in the experiments wherein $^{125}$I labeled TGF-$β_1$ was reacted with PSK, the reaction mixture was applied on a gel filtration chromatography column, and the radioactivities in fractions were measured as carried out in Example 2.

The results were shown in FIG. 2 (groups to which only TGF-$\beta_1$ was added) and FIG. 3 (groups to which PSK and TGF-$\beta_1$ were added). In the control groups (FIG. 2), i.e., the groups to which only TGF-$\beta_1$ was added, the radioactivities were eluated mainly in fraction number 40 (molecular weight=about 25000, i.e., the molecular weight of the active TGF-$\beta$). In the groups wherein PSK was reacted (FIG. 3), the radioactivities were observed in the fraction numbers 10 to 18 (eluating position of PSK). Therefore, the results of gel filtration chromatography show the binding of PSK and TGF-$\beta$.

Example 3

The fetal mink lung cell line Mv1Lu (Dainippon Pharmaceutical) or the mouse T cell line CTLL-2 (Rikagaku Kenkyusho) was suspended in the culture medium as mentioned below so that the concentration became 5×10$^5$ cells/ml, and 100 µl of the suspension was poured in each well of 96-well culture plate (Falcon 3072; Becton-Dickinson Labware, N.J., USA). Then, a TGF-$\beta_1$ solution prepared from the lyophilized human TGF-$\beta_1$ (Takara Shuzo) as in Example 1 was added to each well so that the concentration thereof became 50 ng/ml. The cells were cultured in a 5% $CO_2$ incubator at 37° C. for 48 hours. As the culture medium for the cell line Mv1Lu, Eagle's minimum essential medium containing 10% fetal bovine serum, 2 mM glutamine and 0.1 mM non-essential amino acids was used. As the culture medium for the cell line CTLL-2, the RPMI 1640 medium containing 10% fetal bovine serum, 20 units/ml mouse interleukin-2, and 2 mM glutamine was used. At 4 hours before the end of the cultivation, 15 µl of MTT reagent [i.e., a solution prepared by dissolving 3-(4,5-dimethylthiazol-2-yl)-2,5-diphenyltetrazolium bromide in phosphate buffered physiological saline so that the concentration became 5 mg/ml] was poured to each well. After the cultivation was completed, formazan formed in cells was dissolved in 200 µl of 40 mM HCl acidic isopropanol, and the absorbance at 570 nm was measured by a plate reader (control culture test).

Further, the experiments wherein a PSK solution prepared as in Example 1 was added to said culture system were carried out.

Figure 4:
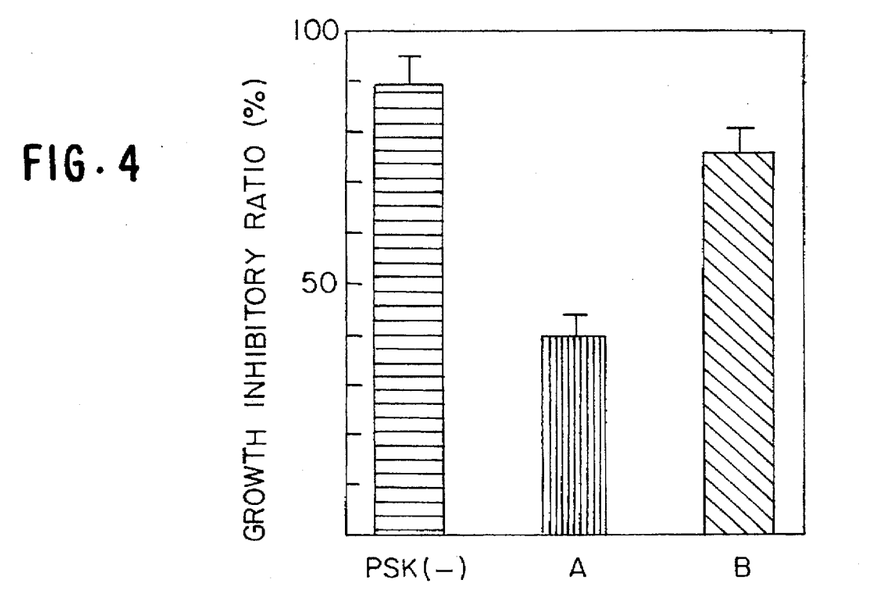
FIG. 4 is a graph showing the restoring effect of PSK to the growth inhibition by TGF-$β_1$, in the experiments wherein PSK and TGF-$β_1$ were added to the in vitro growing system of the fetal mink lung cell line Mv1Lu, as carried out in Example 3.

In the test (A) for the fetal mink lung cell line Mv1Lu, the PSK solution was added to each well to which the Mv1Lu suspension had been poured as in the control culture test, so that the concentration of PSK became 100 µg/ml, then TGF-$\beta_1$ was added so that the concentration became 50 ng/ml, and thereafter the procedure of the control culture test was repeated. In the test (B) for the fetal mink lung cell line Mv1Lu, after the PSK solution was added as in the test (A), the cells were thoroughly washed with the culture medium to remove unbound PSK, then TGF-$\beta_1$ was added so that the concentration became 50 ng/ml, and thereafter the procedure of the control culture test was repeated. The results are shown in FIG. 4. In FIG. 4, "PSK(−)" is the results of the control culture test wherein PSK was not added, "A" is the results of the test (A) wherein after PSK was added, TGF-$\beta_1$ was added without washing, and "B" is the results of the test (B) wherein after PSK was added and the unbound PSK was removed by washing, TGF-$\beta_1$ was added.

Figure 5:
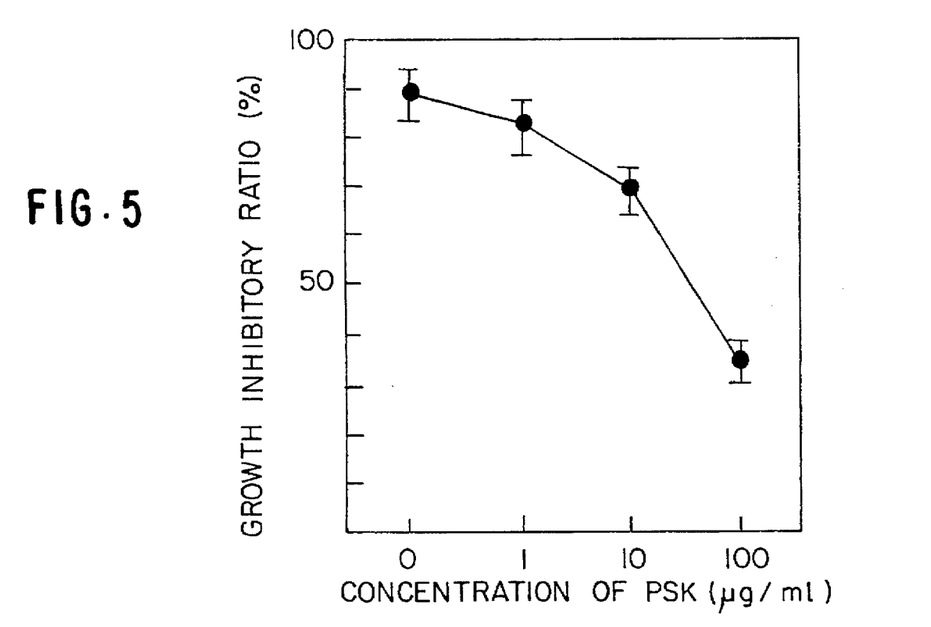
FIG. 5 is a graph showing a dose-dependency of the restoring effect of PSK to the growth inhibition by TGF-$β_1$, in the experiments wherein PSK and TGF-$β_1$ were added to the in vitro growing system of the fetal mink lung cell line Mv1Lu, as carried out in Example 3.

Further, the procedure of the test (A) was repeated, except that PSK was added so that the concentration thereof became 1 µg/ml, 10 µg/ml, and 100 µg/ml. The results are shown in FIG. 5.

Figure 6:
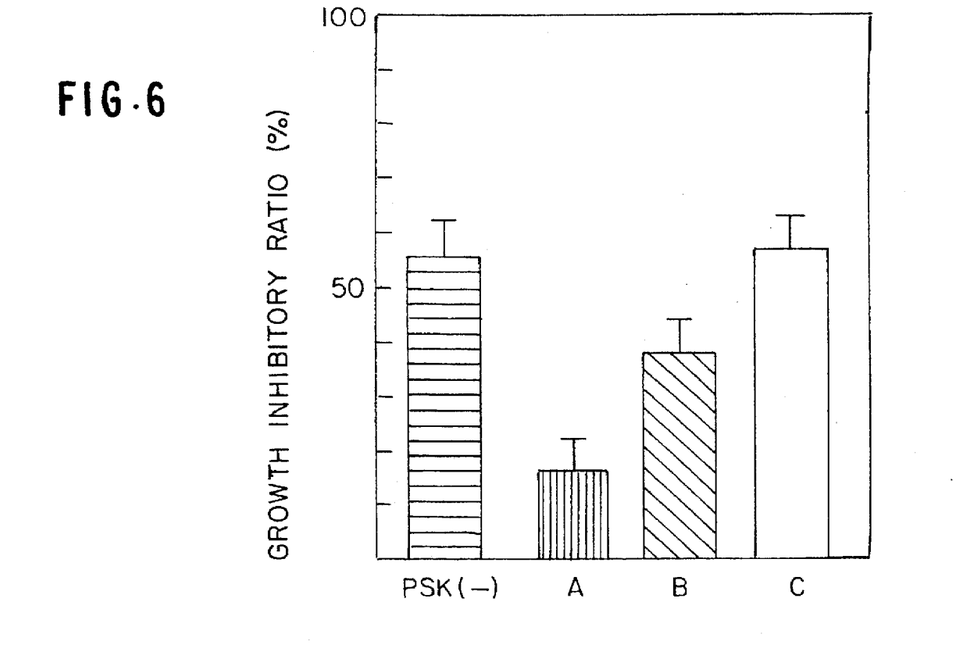
FIG. 6 is a graph showing the restoring effect of PSK to the growth inhibition by TGF-$β_1$, in the experiments wherein PSK and TGF-$β_1$ were added to the in vitro growing system of the mouse T cell line CTLL-2, as carried out in Example 3.

In the test (A) for the mouse T cell line CTLL-2, the PSK solution was added to each well to which the CTLL-2 suspension had been poured as in the control culture test, so that the concentration of PSK became 100 µg/ml, then TGF-$\beta_1$ was added so that the concentration became 50 ng/ml, and thereafter the procedure of the control culture test was repeated. In the test (B) for the mouse T cell line CTLL-2, TGF-$\beta_1$ was added to each well to which the CTLL-2 suspension had been poured as in the control culture test, so that the concentration became 50 ng/ml, then the PSK solution was added so that the concentration of PSK became 100 µg/ml, and thereafter the procedure of the control culture test was repeated. In the test (C) for the mouse T cell line CTLL-2, after the PSK solution was added as in the test (A), the cells were thoroughly washed with the culture medium to remove unbound PSK, then TGF-$\beta_1$ was added so that the concentration became 50 ng/ml, and thereafter the procedure of the control culture test was repeated. The results are shown in FIG. 6. In FIG. 6, "PSK(−)" is the results of the control culture test wherein PSK was not added, "A" is the results of the test (A) wherein after PSK was added, TGF-$\beta_1$ was added without washing, "B" is the results of the test (B) wherein after TGF-$\beta_1$ was added, PSK was added without washing, and "C" is the results of the test (C) wherein after PSK was added and the unbound PSK was removed by washing, TGF-$\beta_1$ was added.

Figure 7:
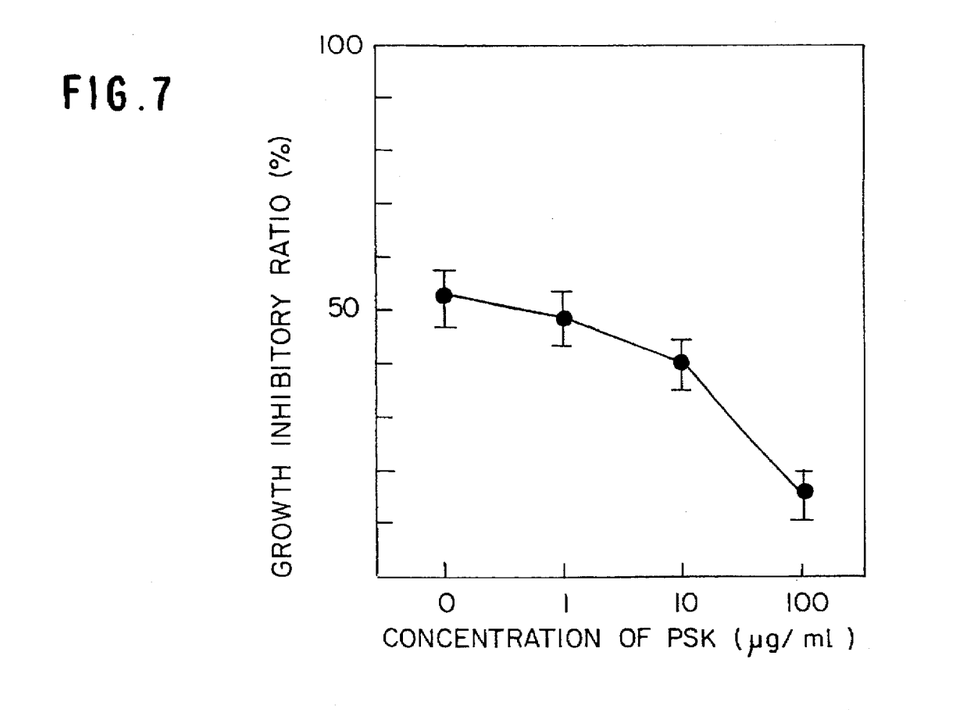
FIG. 7 is a graph showing a dose-dependency of the restoring effect of PSK to the growth inhibition by TGF-$β_1$, in the experiments wherein PSK and TGF-$β_1$ were added to the in vitro growing system of the mouse T cell line CTLL-2, as carried out in Example 3.

Further, the procedure of the test (A) was repeated, except that PSK was added so that the concentration thereof became 1 µg/ml, 10 µg/ml, and 100 µg/ml. The results are shown in FIG. 7.

In FIGS. 4 to 7, growth inhibitory ratio (%) was calculated from the equation (II):

$$\text{Growth inhibitory ratio } (\%) = (Ac - Ap)/Ac \times 100 \quad \text{(II)}$$

wherein Ac is an absorbance at 570 nm of formazan formed in the control culture test, Ap is an absorbance at 570 nm of formazan formed in the test wherein TGF-$\beta_1$ was added, or TGF-$\beta_1$ and PSK were added.

As shown in the above Figures, the growth of the cell lines was inhibited by TGF-$\beta_1$. When PSK was added before adding TGF-$\beta_1$, the inhibitory action by TGF-$\beta_1$ was lowered in each cell line. Further, the function of PSK is dose-dependent. Therefore, it is manifest that the direct binding of PSK and TGF-$\beta_1$ brings about the reduction of TGF-$\beta_1$ activity.

Example 4

Figure 8:
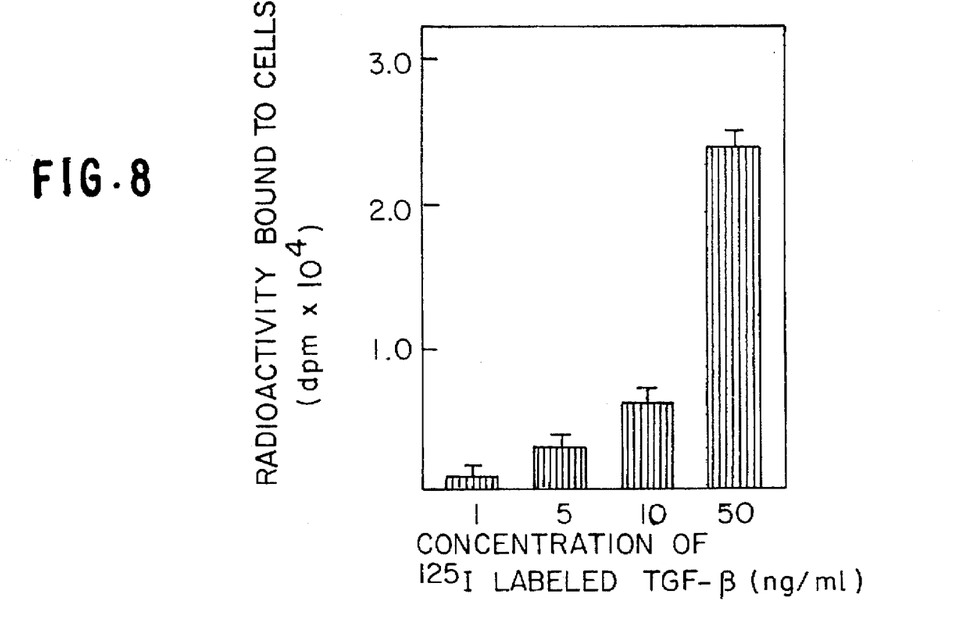
FIG. 8 is a graph showing a dose-dependency of the TGF-$β_1$ binding to the fetal mink lung cell line Mv1Lu, in the experiments wherein the $^{125}$I labeled TGF-$β_1$ was added to the in vitro binding assay system of the cell line Mv1Lu, as carried out in Example 4.
Figure 9:
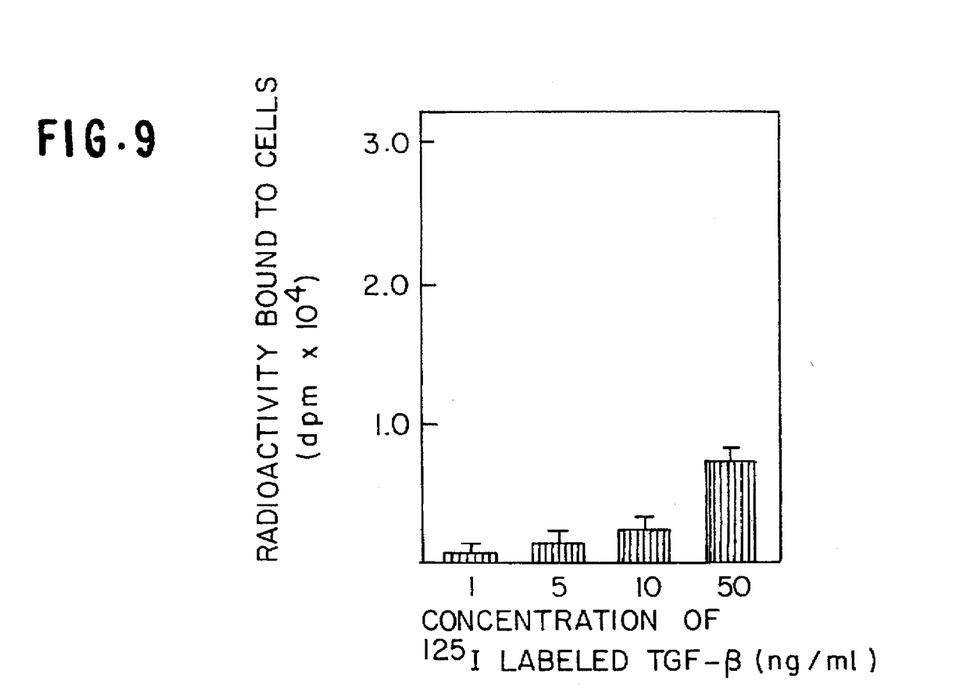
FIG. 9 is a graph showing a dose-dependency of the TGF-$β_1$ binding to the mouse T cell line CTLL-2, in the experiments wherein the $^{125}$I labeled TGF-$β_1$ was added to the in vitro binding assay system of the cell line CTLL-2, as carried out in Example 4.

The fetal mink lung cell line Mv1Lu (Dainippon Pharmaceutical) or the mouse T cell line CTLL-2 (Rikagaku Kenkyusho) was suspended in the culture medium for the binding tests [i.e., Dulbecco's minimum essential medium containing 0.1% bovine serum albumin and 25 mM Hepes] so that the concentration became $1 \times 10^6$ cells/ml. The cells were precultured in a 5% $CO_2$ incubator at 37° C. for 2 hours. After the cultivation was completed, the cells were washed with the culture medium for the binding tests three times to adjust the cell concentration to $1 \times 10^6$ cells/ml. To the resulting cell suspension, a solution of $^{125}$I labeled human recombinant TGF-$\beta_1$ (74–167 TBq/mmol; Daiichi Kagaku Yakuhin) prepared as in Example 2 so that the concentration thereof became 1 ng/ml, 5 ng/ml, 10 ng/ml, or 50 ng/ml. The cells were cultured at 22° C. for 3 hours. After the cells were washed by centrifuging, radioactivities bound to cells were measured by a gamma counter. Non-specific bindings of cells were examined in the presence of non-labeled TGF-$\beta_1$. The results are shown in FIG. 8 (the fetal mink lung cell line Mv1Lu) and FIG. 9 (the mouse T cell line CTLL-2). As clear from FIGS. 8 and 9, the radioactivity bound to cells were dependent on the concentration of TGF-$\beta_1$ added.

Figure 10:
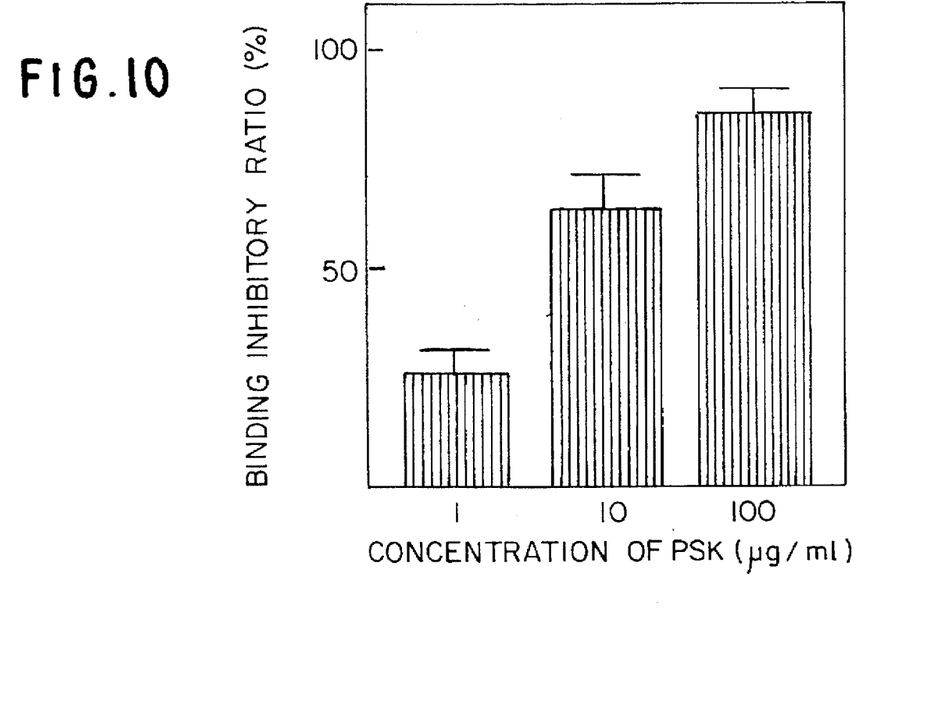
FIG. 10 is a graph showing a dose-dependency of the cell binding inhibitory by PSK, in the experiments wherein the $^{125}$I labeled TGF-$β_1$ and PSK were added to the in vitro binding assay system of the fetal mink lung cell line Mv1Lu, as carried out in Example 4.

Then, the experiments wherein PSK was added to the above cultivating system were carried out. More particularly, PSK was added to the above cell suspension so that the concentration of PSK became 1 µg/ml, 10 µg/ml, or 100 µg/ml, then TGF-$\beta_1$ was added without washing so that the concentration of TGF-$\beta_1$ became 50 ng/ml, and thereafter the above procedure was repeated. The results are shown in FIG. 10 (the fetal mink lung cell line Mv1Lu) and FIG. 11 (the mouse T cell line CTLL-2). When PSK was added before TGF-$\beta_1$ was added, the binding of TGF-$\beta_1$ to the cells was inhibited. The function of PSK was dose-dependent. Therefore, it is clear that the action of PSK is caused by the direct binding to TGF-$\beta_1$.

Figure 11:
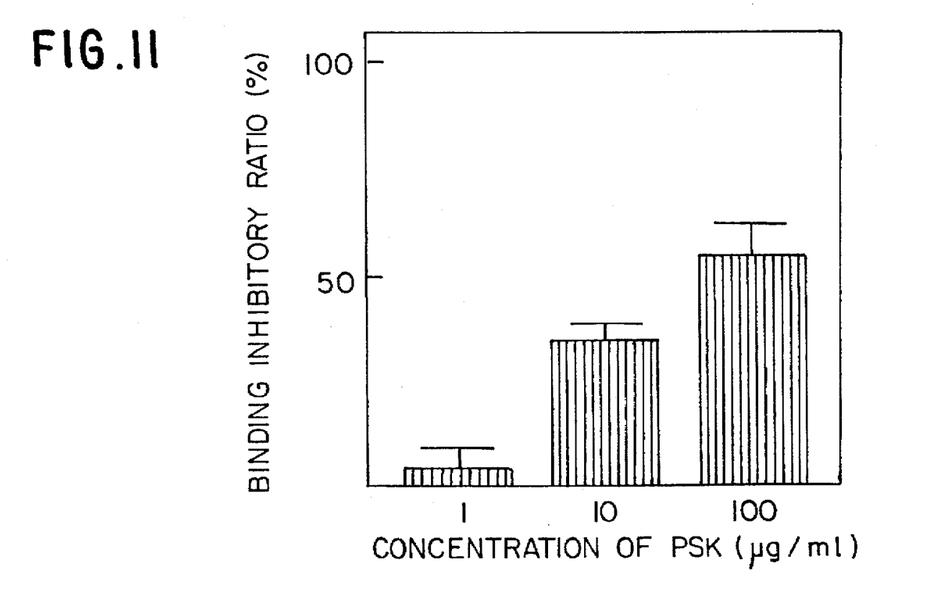
FIG. 11 is a graph showing a dose-dependency of the cell binding inhibitory by PSK, in the experiments wherein the $^{125}$I labeled TGF-$β_1$ and PSK were added to the in vitro binding system of the mouse T cell line CTLL-2, as carried out in Example 4.

In FIGS. 10 and 11, the binding inhibitory ratio (%) was calculated from the equation (III):

$$\text{Binding inhibitory ratio } (\%) = (Rc - Rp)/Rc \times 100 \quad \text{(III)}$$

wherein Rc is the radioactivity (dpm) when PSK is not added, and Rp is the radioactivity (dpm) when PSK is added.

Example 5

Figure 12:
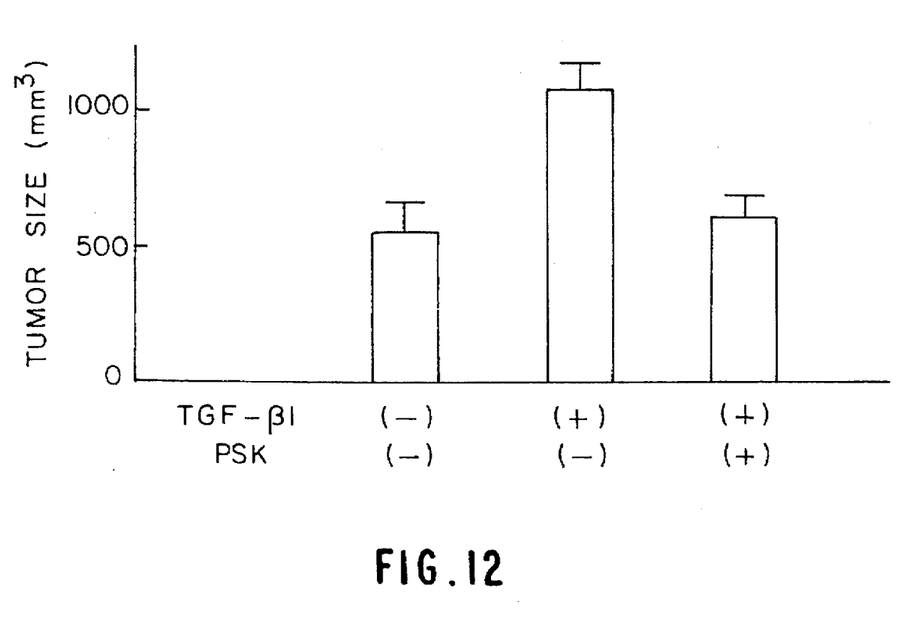
FIG. 12 is a graph showing the effect by the differences of the tumor sizes, when TGF-$β_1$ and/or PSK were administered to the leukemic cells-implanted mice, as carried out in Example 5.

EL4 leukemia cells (distributed from Microbiology department in National Defense Medical College, Saitama, Japan) were subcutaneously implanted to 8-week-old female C57BL/6 mice (Charles River Japan) (a group consists of 5 mice) in an amount of $1 \times 10^6$ cells. The size of the tumor was measured by a slide caliper with time. The TGF-$\beta_1$ solution prepared as in Example 1 was intraperitoneally administered at a dose of 1 μg per a mouse for 4 days in succession after the implantation of the tumor. Further, the PSK solution prepared as in Example 1 was intraperitoneally administered at a dose of 100 mg/kg for 4 days in succession after the implantation of the tumor. The tumor sizes at the 9th day after the implantation are shown in FIG. 12, wherein "(−)" means not-administered, and "(+)" means administered. In comparison with the non-treatment group, the growth promotion of the tumor was clearly observed in the group wherein TGF-$\beta_1$ was administered, but PSK was not administered, whereas in the group wherein TGF-$\beta_1$ and PSK were administered, no promotion was observed and the size was almost same as that in the non-treatment group. When PSK was added to the group wherein TGF-$\beta_1$ was not administered, the growth of the tumor was not influenced. Therefore, it is apparent that the function of PSK is caused by the direct action to TGF-$\beta_1$.

As explained above, the protein-bound polysaccharide used in the present invention can selectively inhibit only the biological activities of TGF-$\beta_1$ and/or PDGF, without an allergic reaction when an antibody preparation (anti-TGF-$\beta_1$ or PDGF antibody) is administered in a living body, or without lowering the activity of the antibody preparation when a neutralizing antibody to the preparation is formed.

Further, the protein-bound polysaccharide used in the present invention has been clinically used as a carcinostatic agent and proved to hardly produce side-effects.

Although the present invention has been described with reference to specific embodiments, various changes and modifications obvious to those skilled in the art are deemed to be within the sprit, scope, and concept of the invention.

We claim:

1. A method for treatment or prevention of a disease or condition directly or indirectly caused by a growth factor selected from the group consisting of transforming growth factor-β (TGF-β) and platelet-derived growth factor (PDGF), comprising administering to a mammal an effective amount of a protein-bound polysaccharide which is obtained from a fungus belonging to Coriolus, and which contains about 18 to 38% by weight of protein, said disease or condition being fibroid lung, hepatic fibrosis, glomerulonephritis, or scleroderma.

2. The method according to claim 1, wherein the protein-bound polysaccharide is an extract from mycelia, broth, or fruit bodies obtained by culturing a fungus belonging to Coriolus.

3. The method according to claim 1, wherein the protein-bound polysaccharide is prepared by extracting mycelia of Coriolus versicolor (Fr.) Quél with water, purifying and then drying a resulting extract.

* * * * *